(12) United States Patent
Brendel et al.

(10) Patent No.: US 9,566,578 B2
(45) Date of Patent: Feb. 14, 2017

(54) HYDROCHLORIC ACID STRIPPING PROCESS FOR IONIC LIQUID REGENERATION PROCESS

(71) Applicant: UOP LLC, Des Plaines, IL (US)

(72) Inventors: Michael Brendel, Chicago, IL (US); Avram M. Buchbinder, Chicago, IL (US); Paul Olson, Mount Prospect, IL (US); Susie C. Martins, Carol Stream, IL (US); Kaitlin M. DeSalvo, Chicago, IL (US); Douglas A. Nafis, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/567,844

(22) Filed: Dec. 11, 2014

(65) Prior Publication Data

US 2016/0167034 A1 Jun. 16, 2016

(51) Int. Cl.
| | | |
|---|---|---|
| *B01J 31/40* | (2006.01) | |
| *B01J 38/68* | (2006.01) | |
| *C07F 9/02* | (2006.01) | |
| *B01J 31/02* | (2006.01) | |
| *C07F 9/54* | (2006.01) | |

(52) U.S. Cl.
CPC ......... *B01J 31/4069* (2013.01); *B01J 31/0298* (2013.01); *B01J 38/68* (2013.01); *C07F 9/025* (2013.01); *C07F 9/5407* (2013.01); *B01J 2231/44* (2013.01); *B01J 2531/002* (2013.01); *B01J 2531/008* (2013.01)

(58) Field of Classification Search
None
See application file for complete search history.

(56) References Cited

U.S. PATENT DOCUMENTS

| | | | |
|---|---|---|---|
| 7,732,364 B2 | 6/2010 | Chang et al. | |
| 8,597,517 B2 | 12/2013 | Guzman Lucero et al. | |
| 8,779,220 B2 | 7/2014 | Noelke et al. | |
| 9,079,176 B1* | 7/2015 | Smith | B01J 31/4053 |
| 9,096,618 B1* | 8/2015 | Martins | C07F 7/0801 |
| 9,120,092 B1* | 9/2015 | Broderick | B01J 31/4053 |
| 2007/0142216 A1* | 6/2007 | Harris | B01J 27/125 502/53 |
| 2012/0165593 A1* | 6/2012 | Liu | B01J 31/0278 585/719 |
| 2013/0303358 A1 | 11/2013 | Elomari et al. | |
| 2013/0331625 A1* | 12/2013 | Liu | B01J 31/0278 585/315 |
| 2014/0005459 A1 | 1/2014 | Zhan et al. | |
| 2014/0171710 A1 | 6/2014 | Mahieux et al. | |

FOREIGN PATENT DOCUMENTS

WO 2014184803 A2 11/2014

OTHER PUBLICATIONS

PCT Search Report dated Mar. 24, 2016 for corresponding PCT International Application No. PCT/US2015/063677.

* cited by examiner

*Primary Examiner* — Rosalynd Keys

(57) ABSTRACT

A method for regenerating deactivated acidic ionic liquid is described. The method involves reducing a level of free hydrochloric acid in the deactivated acidic ionic liquid in a removal zone using at least one of heat, a stripping fluid, reduced pressure, and liquid-liquid extraction to form a deactivated acidic ionic liquid having a reduced level of free hydrochloric acid; and regenerating the deactivated acidic ionic liquid having the reduced level of free hydrochloric acid.

20 Claims, 1 Drawing Sheet

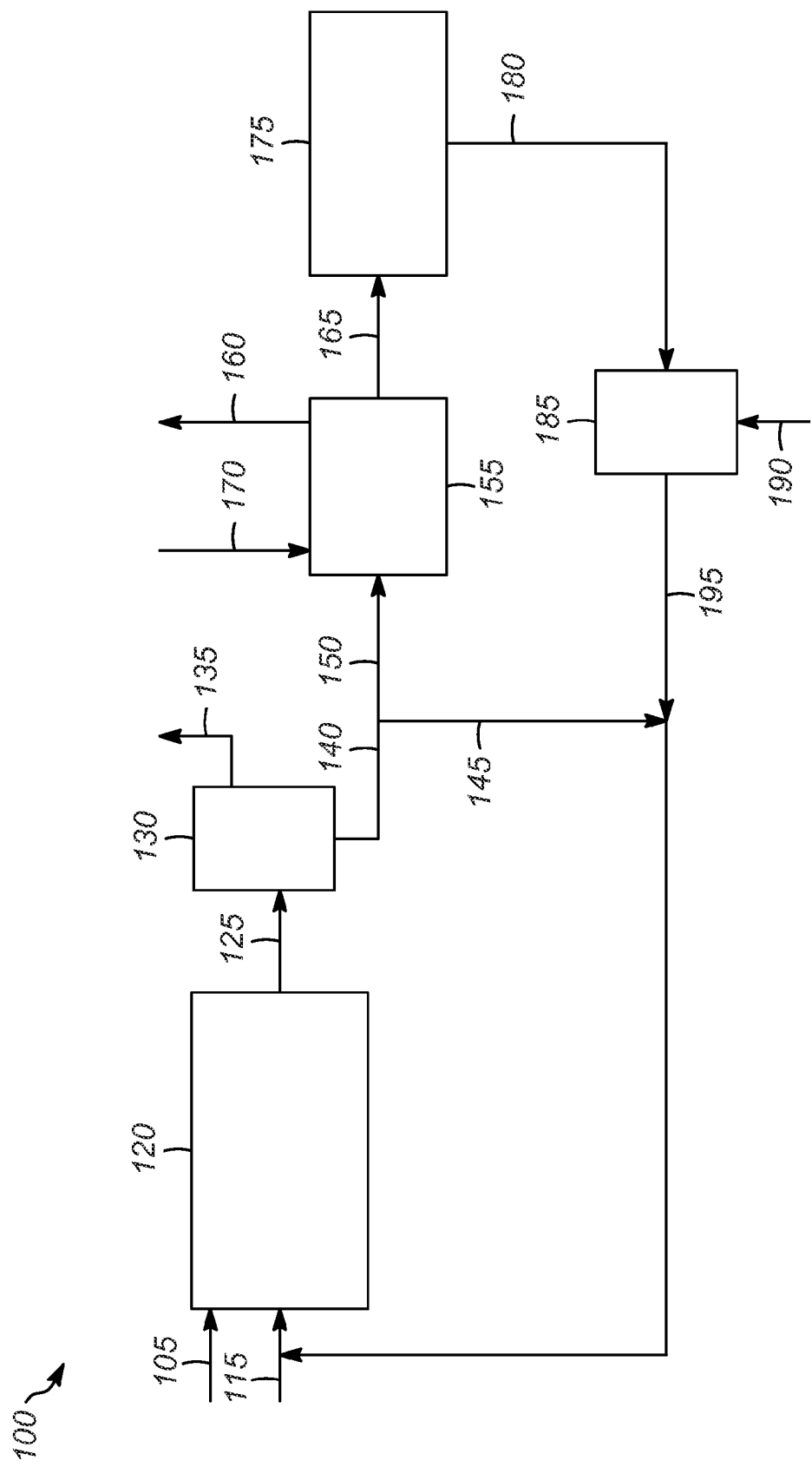

HYDROCHLORIC ACID STRIPPING PROCESS FOR IONIC LIQUID REGENERATION PROCESS

BACKGROUND OF THE INVENTION

Commercially, the alkylation of isoparaffins is catalyzed by acids such as sulfuric acid and hydrofluoric acid. Conjunct polymer (acid soluble oils, (ASO) also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

There has been a move to replace the use of sulfuric acid and hydrofluoric acid with more environmentally friendly materials.

One such process utilizes acidic ionic liquids as catalysts in hydrocarbon conversion processes, such as alkylation, isomerization, disproportionation, reverse disproportionation, and oligomerization. Conjunct polymers are byproducts of the hydrocarbon reaction using ionic liquids, and they form a complex with the ionic liquid catalyst. The ionic liquid catalyst loses its effectiveness over time as the amount of conjunct polymer increases. It must then either be replaced or regenerated. Because ionic liquids are typically fairly expensive, processes for regenerating the ionic liquid catalysts are needed.

A variety of methods for regenerating ionic liquids have been developed. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the CP to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][$Al_2Cl_7$]) containing the conjunct polymer followed by an inert hydrocarbon. After a given time of mixing, the hydrocarbon layer would be separated, resulting in a regenerated ionic liquid. The solid residue would be converted to catalytically active ionic liquid by adding $AlCl_3$. See e.g., U.S. Pat. No. 7,737,363 and U.S. Pat. No. 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

All of these regeneration approaches have drawbacks. Many of them cannot achieve above 90% conversion of the conjunct polymer, which then builds up in the process. Of those that can provide high levels of conversion, hydrogenation of the spent ionic liquid with supported (e.g., U.S. Pat. No. 7,691,771) and unsupported (e.g., U.S. Pat. No. 7,678,727) hydroprocessing catalysts may result in the active catalytic metals being extracted into the ionic liquid phase. Many catalyst supports also react irreversibly with the chloroaluminate anion of the ionic liquid. Although the use of metallic aluminum for regeneration (e.g., U.S. Pat. No. 7,995,495) is effective, it introduces undesirable solids handling issues into the refinery. Finely divided aluminum is pyrophoric and presents safety issues in a refining environment. This approach also results in the creation of additional $AlCl_3$, which has to be removed from the ionic liquid phase (e.g., U.S. Pat. No. 7,754,636) to avoid building up to a molar ratio relative to the ionic liquid cation at which solids will start precipitating out of solution and cause plugging issues. Electrochemical approaches (e.g., U.S. Pat. No. 8,524,623) are not economically viable at commercial scales.

When the ionic liquid is regenerated using a reducing agent or a base reagent, the reducing agent or base reagent strips the ionic liquid of acid sites, ultimately reducing the affinity of the conjunct polymer with the ionic liquid. However, if solubilized HCl remains in the ionic liquid, an excess amount of reducing agent or base reagent is required to titrate all of the acid sites, resulting in increased material costs.

Therefore, there is a need for improved methods of regenerating deactivated ionic liquid.

SUMMARY OF THE INVENTION

One aspect of the invention involves a method for regenerating deactivated acidic ionic liquid. In one embodiment, the method involves reducing a level of free hydrochloric acid in the deactivated acidic ionic liquid in a removal zone using at least one of heat, a stripping fluid, reduced pressure, and liquid-liquid extraction to form a deactivated acidic ionic liquid having a reduced level of free hydrochloric acid; and regenerating the deactivated acidic ionic liquid having the reduced level of free hydrochloric acid.

BRIEF DESCRIPTION OF THE DRAWING

The FIGURE illustrates one embodiment of a method for regenerating deactivated ionic liquid according to the present invention.

DETAILED DESCRIPTION OF THE INVENTION

The present invention meets this need by providing a method for reducing the level of free HCl in the deactivated ionic liquid containing the conjunct polymer before regenerating the ionic liquid. There are several methods for reducing the level of free HCl, including one or more of heating the deactivated acidic ionic liquid, introducing a stripping fluid into the removal zone, reducing the pressure of the removal zone, and using liquid-liquid extraction. Once the free HCl is removed, the deactivated ionic liquid catalyst can be regenerated using known regeneration methods. By removing the free HCl, the amount of regenerant, for instance a reducing agent or base, needed to titrate the acid sites is reduced.

By deactivated ionic liquid catalysts containing conjunct polymer, we mean acidic ionic liquid catalysts that have been used in hydrocarbon conversion processes, and in which conjunct polymers have formed. By conjunct polymer, we mean the materials containing olefinic, conjugated and cyclic hydrocarbons that form as a byproduct of various hydrocarbon conversion processes, including but not limited to alkylation, oligomerization, isomerization, disproportionation, and reverse disproportionation.

By acidic ionic liquid, we mean an ionic liquid capable of catalyzing reactions typically carried out with an acid. As known in the art, acids such as sulfuric acid and hydrofluoric acid are often used to catalyze these reactions. These reactions include, e.g. alkylation, oligomerization, isomerization, disproportionation, and reverse disproportionation. Oftentimes the acids employed in these reactions have Hammett acidity functions ($H_0$) less than 7, or less than 5, or less than 3, or less than 0, or less than −3, or less than −5, or less than −7, or less than −9. Addition of an exogenous acid is acceptable, provided the Hammett acidity function ($H_0$) of the added acid is less than 7 within the ionic liquid, or less than 5, or less than 3, or less than 0, or less than −3, or less than −5, or less than −7, or less than −9. Acidic chloroaluminate-containing ionic liquids have a molar ratio of Al to cation greater than 1.

By free HCl we mean HCl that is physically dissolved, associated or otherwise mixed into the ionic liquid and excluding HCl that is strongly bound to spent ionic liquid such that it can be removed only by a regeneration process.

By stripping fluid, we mean any liquid, gas, supercritical fluid or combination thereof that is capable of removing the free HCl. The stripping fluid can be a pure substance or a mixture. Preferably, the stripping fluid does not react with the ionic liquid or with HCl.

By the term about, we mean within 10% of the specified value, or within 5%, or within 1%.

In the process 100 illustrated in the FIGURE, one or more hydrocarbon feed streams 105 and ionic liquid stream 115 are introduced into the reaction zone 120 where the feed reacts to form products. The effluent 125 includes the reaction products, unreacted feed, and ionic liquid catalyst.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

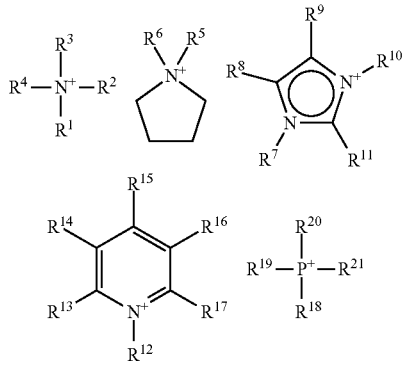

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable. Lactamium based ionic liquids can also be used, such as those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Alkyl Lactam Based Ionic Liquids, filed May 6, 2014, each of which is incorporated herein by reference.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlC_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The effluent 125 is sent to a separation zone 130 where it is separated into a hydrocarbon stream 135 and an ionic liquid stream 140. The separation can be a gravity separation, or any other known separation process for separating an ionic liquid phase from a hydrocarbon phase.

The hydrocarbon stream 135 can be sent for further separation into products and unreacted feed as desired (not shown).

A portion 145 of the ionic liquid stream 140 can be recycled to the reaction zone 120. Another portion 150 of the ionic liquid stream 140 can be sent to the HCl removal zone 155.

One method for reducing the level of free HCl in the deactivated ionic liquid involves heating the deactivated ionic liquid in the removal zone 155. The ionic liquid is heated to a temperature at or above which the HCl will gas off but below the decomposition temperature of the ionic liquid. HCl will gas off at about 100° C. A stream 160 containing the HCl removed from the ionic liquid is removed from the removal zone 155. The effluent 165 from the removal zone 155 has a lower level of free HCl than the incoming portion 150 of ionic liquid stream 140.

The heat can be provided using any known method for heating the ionic liquid including but not limited to, steam, electricity, and a heat transfer fluid. In some embodiments, the removal zone 155 is a stripping column.

In some embodiments, in addition to heating the ionic liquid, a stripping fluid 170 is introduced into the removal zone. The stream 160 of stripping fluid leaving the removal zone is rich in HCl. The stripping fluid can be one or more nitrogen, carbon dioxide, hydrogen, hydrocarbons, such as methane, ethane, propane, fuel gas, n-butane, isobutane, isopentane, pentane, naphtha, and aromatics, or carbon dioxide, carbon monoxide, synthesis gas and combinations thereof.

Another method of reducing the level of free HCl in the deactivated ionic liquid is reducing the pressure in the removal zone 155 compared with the upstream process, such as the separation zone 130. The reduced pressure will flash the HCl. In some embodiments, the pressure will be reduced to less than 1379 kPa (g) (200 psig), or 1034 kPa (g) (150 psig), or 689 kPa (g) (100 psig), or 345 kPa (g) (50 psig). Vacuum pressures can be used, although it would be more expensive.

Alternatively, a stripping fluid 170 can be introduced into the removal zone 155 without heating. The stream 160 leaving the removal zone will be rich in HCl.

In an alkylation process, in the case of the stripping or depressurizing methods where the HCl rich stream 160 is in the gas phase and the pressure is too low to be easily recycled to the alkylation reaction zone 120, stream 160 could be sent to an HCl recovery zone (not shown) where it is reacted with a slip-stream of the olefin feed to the alkylation reaction zone 120 over a catalyst to form a butyl chloride that can be recovered as a liquid and sent back to the alkylation reaction zone 120.

Another method for removing the free HCl is using liquid-liquid extraction. Here the stream 170 is an extraction solvent stream. The extraction solvent stream used to remove the free HCl can be immiscible in the ionic liquid, or it could be partially miscible. By partially miscible, we mean that, in some composition ranges of a binary mixture of the extraction solvent and the ionic liquid, one liquid phase is formed, while at other composition ranges two liquid phases will form. The HCl should be at least partially soluble in the extraction solvent, for example, at least about 200 wppm, or at least about 1000 wppm. Suitable extraction solvents for liquid-liquid extraction include, but are not limited to, at least one hydrocarbon, including paraffins, isoparaffins, naphthenes, and aromatics. In some embodiments the liquid-liquid extraction step can use an extraction solvent to ionic liquid ratio of less than about 15:1 by volume, or less than about 10:1 by volume, or less than about 4:1 by volume. Multiple stages may be used in the liquid-liquid extraction. Methods for liquid-liquid extraction include stirred vessels, vessels with trays, stirred vessels in series, or other extraction methods known in the art. In some embodiments, the temperature of the liquid-liquid extraction is in the range of about 0° C. to about 200° C., preferably about 20° C. to about 80° C. The pressure of the liquid-liquid extraction should be sufficient to maintain two liquid phases. Exemplary pressure ranges are less than about 5.5 MPa(g) (800 psig), or less than about 4.1 MPa(g) (600 psig), or less than about 2.8 MPa(g) (400 psig). The stream 160, an extraction solvent stream rich in HCl, is removed from the HCl removal zone. In this case, where the process is an alkylation process and the solvent is isobutane, the HCl rich stream 160 could be sent back to an alkylation zone debutanizer column, or combined with another existing isobutane/HCl process stream that is at lower pressure. If the solvent is not already a process stream in the alkylation reaction zone, it could be sent to an HCl recovery zone (not shown).

The effluent 165 from the removal zone 155 is sent to the ionic liquid regeneration zone 175 where it undergoes a suitable regeneration process. The regenerated ionic liquid stream 180 can be recycled to the reaction zone 120. It can optionally be combined with the portion 145 of the ionic liquid stream 140. The regenerated ionic liquid stream 180 is sent to a re-acidification zone 185 where it is re-acidified by addition of a stream 190 of HCl or a precursor which reacts to form HCl such as a chloroalkane. In some embodiments, stream 190 is the HCl rich stream 160 from the removal zone 155. The stream 160/190 could be a gas or a liquid. The acidified regenerated ionic liquid stream 195 is recycled to the reaction zone 120. The acidified ionic liquid stream 195 can be combined with the portion 145, if desired. Alternatively, the regenerated ionic liquid stream 180 can be combined with the portion 145 before being sent to the re-acidification zone 185. Alternatively, the re-acidifying step may take place in the reaction zone 120.

The amount of free HCl in the effluent 165 is at least about 50% less than the incoming portion 150, or at least about 60% less, or at least about 70% less, or at least about 80% less, or at least about 90% less. The total amount of free and associated HCl can be measured by titration with stoichiometric amounts of a base. In some embodiments, a silane or borane compound can be used as the titrant. See e.g., U.S. application Ser. No. 14/270,033, METHOD FOR QUANTITATION OF ACID SITES IN ACIDIC IONIC LIQUIDS USING SILANE AND BORANE COMPOUNDS, filed May 5, 2014. Many titrants, including a silane or a borane compound, will titrate both the free HCl that may be removed by stripping or extracting as well as HCl that is associated with the conjunct polymer. The HCl that is associated with the conjunct polymer will not easily be removed by a stripping or extracting process prior to regeneration. The total amount of HCl including free and associated HCl in the effluent 165, as measured by the amount of titrant consumed, is less than the amount of free and associated HCl in the ionic liquid stream 150. The amount of decrease of free HCl in stream 165 compared to stream 150 depends on the extraction conditions and on the amount of acid sites associated with the conjunct polymer. In most embodiments, the amount of free HCl in stream 165 is at least about 3% less than the amount in stream 150 or at least about 7% less. The amount of free HCl removed in the HCl removal zone 155 can be determined, for instance, by measuring a difference in the amount of titrant consumed in the two streams or by measuring the chloride content of the stream 160 of the stripping fluid or extraction solvent leaving the HCl removal zone.

The HCl can optionally be recovered from the HCl rich stripping fluid or extraction solvent stream 160. The recovered HCl can optionally be used to reactivate the regenerated ionic liquid catalyst if needed, or fed to the hydrocarbon conversion zone 120. In some embodiments, the recovery of HCl from the HCl rich stripping fluid or extraction solvent stream 160 is not necessary and the entire stream is fed to the hydrocarbon conversion zone 120 or contacted with the regenerated ionic liquid catalyst to reactivate it.

The process can be used with any regeneration process which would benefit from having a reduced level of free HCl.

For purposes of example only, the process will be described combined with the regeneration processes described in U.S. application Ser. No. 14/269,943, entitled REGENERATION OF AN ACIDIC CATALYST BY SILANE ADDITION, filed May 5, 2014, and Ser. No. 14/269,978, entitled REGENERATION OF AN ACIDIC CATALYST BY BORANE ADDITION, filed May 5, 2014. However, those of skill in the art will understand that it could be used with other regeneration processes.

The processes described in U.S. application Ser. Nos. 14/269,943 and 14/269,978 involve regenerating deactivated acidic ionic liquid catalysts containing conjunct polymer using silane or borane compounds. This regeneration process has a number of advantages. The silane and borane compounds contain no metals and react at mild conditions. The mild operating conditions may result in lower operating costs than processes requiring harsher conditions, as well as lower capital costs because less expensive materials of construction can be used.

The regeneration process involves contacting silane or borane compounds with the deactivated ionic liquid catalyst having the reduced level of free HCl. The silane or borane compounds react with the acid sites of the ionic liquid catalyst. For example, the silane or borane compounds will react with the acidic sites in a halometallate ionic liquid to form silyl or boryl halides. The acid sites that were binding the conjunct polymer are no longer present, which allows the conjunct polymer to be removed.

The conjunct polymer has to be separated from the silyl or boryl compounds so that the silyl or boryl compounds can be regenerated into the initial silane or borane compounds so that they can be reused.

One of the methods of separation described in these applications involves sending a hydrocarbon phase containing the silyl or boryl compounds, as well as solvent (if present), conjunct polymer, hydrogen, and any unreacted silane or borane compounds to a separation zone for separation. The hydrocarbon phase is separated into an overhead stream of hydrogen, a stream of solvent and an unreacted silane or borane compounds, a side stream of silyl or boryl compound, and a bottoms stream of conjunct polymer.

The silane compound can be any compound with a reactive SiH moiety. In some embodiments, the silane compound is an organosilane. There can be one or more silanes. Suitable silane compounds include, but are not limited to, silanes having the formulas: $R_3SiH$, $R_2SiH_2$, $RSiH_3$, or $SiH_4$ where each R is independently selected from hydrocarbons or halides. Examples of suitable silanes include triethylsilane, trimethylsilane, triisopropylsilane, and the like. In some embodiments, the silane can be a silane-containing resin.

The silyl compound will be the reaction product of the silane compound and the acid site ($H^+$) on the conjunct polymer. When the silane has one the formulas above, the silyl compound will have the formula: $R_3SiX$, $R_2SiX_2$, $RsiX_3$, or $SiX_4$, where each R is independently selected from hydrocarbons, and each X is independently selected from halides.

The borane compound can be any borane compound having a reactive B—H bond. In some embodiments, the borane compound is an organoborane. There can be one or more boranes. Suitable borane compounds include, but are not limited to, boranes having the formulas: $R_2BH$ or where each R is independently selected from hydrocarbons or halides, or $B_2H_6$, or combinations thereof. Examples of suitable boranes include 9-borabicyclo (3,3,1) nonane, trimesitylborane, trisec-butylborane, diborane, and the like. In some embodiments, the borane can be a borane-containing resin.

The boryl compound will be the reaction product of the borane compound and the acid site ($H^+$) on the conjunct polymer. When the borane has the formula $R_2BH$, the boryl compound will have the formula: $R_2BX$, where each R is independently selected from hydrocarbons or halides. When the borane has the formula $B_2H_6$, the boryl compound is a boron halide compound.

The contacting time for silane compounds is typically in the range of about 5 sec to about 1 hr, or about 1 min to about 45 min, or about 1 min to about 30 min, or about 1 min to about 15 min. For borane compounds at room temperature, the reaction is slower than with the silane, e.g., many hours. The contacting time needed is less at elevated temperatures, e.g., less than 2 hr at 60° C.

The contacting typically takes place at a temperature in the range of from about −20° C. to the decomposition temperature of the ionic liquid. A typical temperature range is about 20° C. to about 80° C. In some embodiments, the contacting takes place at room temperature. In some embodiments with borane compounds, the contacting takes place at temperatures in the range of about 40° C. to about 80° C., or about 70° C.

The pressure is typically ambient pressure, although higher or lower pressures could be used if desired.

In some embodiments, the reaction is conducted under an inert gas so that hydrolysis of ionic liquid and/or the silane or borane compounds does not occur. Suitable inert gases include, but are not limited to, nitrogen, helium, neon, argon, krypton, and xenon.

In some embodiments, the volume ratio of the solvent (when present) to the deactivated acidic ionic liquid is in a range of about 0.25:1 to about 10:1.

In some embodiments, the molar ratio of the silane compound to the conjunct polymer is in a range of about 1:1 to about 5:1, or about 2:1 to about 3:1. In some embodiments, the molar ratio of the borane compound to the conjunct polymer is in a range of about 0.5:1 to about 5:1, or about 2:1 to about 3:1. In some embodiments, the silane or borane compound can be present in excess of the amount needed for reaction with the conjunct polymer, and the excess silane or borane compound can act as a solvent. In these cases, the molar ratio of the silane compound or borane compound to the conjunct polymer is more than 5:1, e.g., in the range of 10:1 to about 1000:1.

The contacting step wherein the deactivated ionic liquid is contacted with the silane or borane compound may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants. After contacting the ionic liquid catalyst and the silane or borane compound, two phases result, an ionic liquid catalyst phase containing the ionic liquid catalyst and an organic phase containing the conjunct polymer, the silyl or boryl compound, and solvent, if present.

The contacting can take place in any suitable process, such as solvent extraction, or contacting in one or more mixer/settlers. In the solvent extraction process, a solvent and a silane or borane compound are added to the ionic liquid containing conjunct polymer. The solvent and the silane or borane compound can be pre-mixed and added together, or they can be added separately, either at the same time or sequentially. Solvent is not always necessary, but it will maximize recovery, removal, and separation of the conjunct polymer.

The solvent will depend on the ionic liquid catalyst being regenerated. The solvent can be any solvent which is capable of forming a separate phase from the catalyst phase. There can be one or more solvents. Suitable solvents for halometallate ionic liquids include, but are not limited to, n-paraffins, isoparaffins, and cyclic paraffins, such as $C_4$ to $C_{10}$ paraffins, and aromatic solvents. If the ionic liquid is soluble in hydrocarbons, more polar solvents which are not miscible in the ionic liquid would be used. The use of organic solvents may be less desirable with oxidizing acids.

The silane or borane compound reacts with the acid sites associated with the conjunct polymer and any remaining free acid. After these acid sites are quenched, the conjunct polymer migrates from the ionic liquid phase to the organic phase and can be extracted.

The reaction will proceed simply by contacting the silane or borane compound with the ionic liquid catalyst. However, the mixture can be subjected to high shear mixing to increase the contact between the silane or borane compound and the ionic liquid catalyst.

In a system without high shear mixing or after high shear mixing is ended, the components can separate into two phases based on the density difference between the ionic liquid phase and the organic phase which contains the conjunct polymer. The ionic liquid will settle to the bottom, and the organic phase containing the unreacted silane or borane compounds, the silyl or boryl compounds, and the conjunct polymer will be on top of the ionic liquid layer. Increasing the top layer with additional solvent will increase conjunct polymer recovery. Separation typically takes on the order of a few minutes to hours; it is generally less than about 1 hr.

The ionic liquid can be reactivated by adding an appropriate acid before being returned to the hydrocarbon process. Suitable acids and acid precursors include, but are not limited to, HCl (in some embodiments at least a portion can be from the HCl removed from the ionic liquid), tert-butyl chloride, or 2-chlorobutane. The acid precursor can be any molecule that will break down to form the acid. The acid is optionally recovered in the acid recovery zone (prior to regeneration) and used in the reactivation step. Reactivation of the ionic liquid with acid or acid precursor typically takes about 5 sec to about 30 min. It can be done at a range of temperatures. For convenience, it is typically done at the same conditions as the hydrocarbon conversion process which generates the conjunct polymer.

The organic phase containing the conjunct polymer and the silyl or boryl compound can be sent to a coalescer for further separation.

Typical operating conditions for the coalescer include an operating pressure of about 483 kPa (g) (70 psig) to about 1034 kPa (g) (150 psig), or about 552 kPa (g) (80 psig) to about 931 kPa (g) (135 psig), and a temperature in the range of about 32° C. (90° F.) to about 149° C. (300° F.), or about 38° C. (100° F.) to about 104° C. (220° F.).

Example 1

A spent ionic liquid sample was generated in a continuous motor fuel alkylation process which utilized anhydrous HCl addition as a co-catalyst. The spent ionic liquid was tributylhexylphosphonium-$Al_2Cl_7$ with 5.2 wt % conjunct polymer, as determined by hydrolysis and back extraction with hexane. Titration of a portion of the spent ionic liquid with triethyl silane, as detailed in U.S. application Ser. No. 14/270,033, results in 0.874 mmol of triethylsilane converted per gram of spent IL (Example 1A). The acid sites titrated by triethylsilane include both free HCl as well as HCl that is associated with conjunct polymer and likely requires regeneration to recover. Three additional portions of the spent ionic liquid were separately contacted with different amounts of hexane, stirred for 30 minutes at room temperature, and allowed to settle. For each sample, the ionic liquid containing layer (bottom layer) was sampled, weighed, and then titrated with triethylsilane. Example 1B used a 15:1 volume ratio of hexane to IL, Example 1C used a 10:1 ratio and Example 1D used a 4:1 ratio. In Example 1B 0.799 mmol of triethylsilane converted per gram of spent IL, indicating that 8.6% of the total acid sites were extracted. In Example 1C 0.812 mmol of triethylsilane converted per gram of spent IL, indicating that 7.1% of the total acid sites were extracted. In Example 1D 0.792 mmol of triethylsilane converted per gram of spent IL, indicating that 9.4% of the total acid sites were extracted. From this example, it appears that about 7.1% to about 9.4% of the acid can be extracted using hexane at room temperature with a hexane to ionic liquid volume ratio of 4:1 or greater. At these conditions extraction prior to regeneration with triethylsilane would save about 7.1% to about 9.4% of the regenerant.

| Example | hexane/IL volume ratio in extraction | mmol triethylsilane converted/g IL | % reduction in triethylsilane conversion due to extraction |
|---|---|---|---|
| 1A | No HCBN | 0.874 | — |
| 1B | 15 | 0.799 | 8.6% |
| 1C | 10 | 0.812 | 7.1% |
| 1D | 4 | 0.792 | 9.4% |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for regenerating deactivated acidic ionic liquid catalyst from an ionic liquid catalyzed process, comprising the steps of:

(a) withdrawing an effluent comprising hydrocarbon product and deactivated acidic ionic liquid catalyst from a reaction zone;

(b) separating the effluent from step (a) into at least a hydrocarbon phase and an ionic liquid phase comprising at least a portion of the deactivated acidic ionic liquid catalyst;

(c) directing at least a portion of the ionic liquid phase from step (b) to a hydrochloric acid removal zone;

(d) reducing a level of free hydrochloric acid in the ionic liquid phase from step (b) in the hydrochloric acid removal zone using at least one of heat, a stripping fluid, reduced pressure, and liquid-liquid extraction to form a deacidified ionic liquid phase, wherein the deacidified ionic liquid phase has a reduced level of free hydrochloric acid compared to the free hydrochloric acid in the ionic liquid phase of step (b);

(e) directing the deacidified ionic liquid phase from step (d) to an ionic liquid regeneration zone to produce a regenerated ionic liquid catalyst;

(f) returning the regenerated ionic liquid catalyst to the reaction zone.

2. The method of claim 1 wherein the level of free hydrochloric acid is reduced in step (d) using heat, and wherein reducing the level of free hydrochloric acid from the ionic liquid phase comprises:

heating the ionic liquid phase in the hydrochloric acid removal zone; and withdrawing a stream comprising the removed hydrochloric acid from the hydrochloric acid removal zone.

3. The method of claim 2 wherein the hydrochloric acid removal zone is a stripping column.

4. The method of claim 3 further comprising:

introducing a stripping fluid into the stripping column; and withdrawing a stream of stripping fluid rich in hydrochloric acid from the stripping column.

5. The method of claim 4 wherein the stripping fluid comprises at least one of nitrogen, carbon dioxide, carbon monoxide, hydrogen, hydrocarbons, and combinations thereof.

6. The method of claim 2 wherein the ionic liquid phase is heated using at least one of steam, a heat transfer fluid, and electricity.

7. The method of claim 1 wherein the level of free hydrochloric acid is reduced in step (d) using reduced pressure, and wherein reducing the level of free hydrochloric acid from the ionic liquid phase comprises:

reducing a pressure in the hydrochloric acid removal zone to a pressure less than a pressure in the separating step (b).

8. The method of claim 1 wherein the level of free hydrochloric acid is reduced in step (d) using the stripping fluid, and wherein reducing the level of free hydrochloric acid from the ionic liquid phase comprises:

introducing the stripping fluid into the hydrochloric acid removal zone; and withdrawing a stream comprising the stripping fluid comprising the removed hydrochloric acid.

9. The method of claim 8 wherein the stripping fluid comprises nitrogen, carbon dioxide, carbon monoxide, hydrogen, hydrocarbons, or combinations thereof.

10. The method of claim 1 wherein the level of free hydrochloric acid is reduced in step (d) using liquid-liquid extraction, and wherein reducing the level of free hydrochloric acid in the ionic liquid phase comprises:

contacting an extraction solvent stream lean in hydrochloric acid with the ionic liquid phase in the hydrochloric acid removal zone; and further comprising withdrawing an extraction solvent stream rich in hydrochloric acid from the hydrochloric acid removal zone.

11. The method of claim 10 wherein the extraction solvent stream lean in hydrochloric acid comprises a solvent which is immiscible or partially miscible in the ionic liquid phase and in which the hydrochloric acid is at least partially soluble.

12. The method of claim 10 wherein the extraction solvent stream lean in hydrochloric acid comprises at least one hydrocarbon.

13. The method of claim 1 wherein the deactivated acidic ionic liquid contains conjunct polymer, and wherein regenerating the deacidified ionic liquid phase in step (e) comprises:

contacting the deacidified ionic liquid phase with at least one silane or borane compound, the conjunct polymer reacting with the at least one silane or borane compound resulting in a catalyst phase comprising ionic liquid catalyst and an organic phase containing the conjunct polymer and at least one silyl or boryl compound; and separating the catalyst phase from the organic phase.

14. The method of claim 1 further comprising:

withdrawing a stream comprising removed hydrochloric acid from the hydrochloric acid removal zone in step (d); and recovering hydrochloric acid from the stream comprising removed hydrochloric acid.

15. The method of claim 14 further comprising reactivating the regenerated ionic liquid catalyst with the recovered hydrochloric acid.

16. A method for regenerating deactivated acidic ionic liquid catalyst from an ionic liquid catalyzed process, comprising the steps of:

(a) withdrawing an effluent comprising hydrocarbon product and deactivated acidic ionic liquid catalyst from a reaction zone;

(b) separating the effluent from step (a) into at least a hydrocarbon phase and an ionic liquid phase comprising at least a portion of the deactivated acidic ionic liquid catalyst;

(c) directing at least a portion of the ionic liquid phase from step (b) to a hydrochloric acid removal zone;

(d) reducing a level of free hydrochloric acid in the ionic liquid phase from step (b) in the hydrochloric acid removal zone using at least one of heat, a stripping fluid, reduced pressure, and liquid-liquid extraction to form a deacidfied ionic liquid phase, wherein the deacidified ionic liquid phase has a reduced level of free hydrochloric acid compared to the free hydrochloric acid in the ionic liquid phase of step (b);

(e) withdrawing a stream comprising removed hydrochloric acid from the hydrochloric acid removal zone in step (d);

(f) contacting the deacidified ionic liquid phase from step (d) with at least one silane or borane compound, the conjunct polymer reacting with the at least one silane or borane compound resulting in a catalyst phase comprising ionic liquid catalyst and an organic phase containing the conjunct polymer and at least one silyl or boryl compound; and (g) separating the catalyst phase from the organic phase.

17. The method of claim 16 wherein the level of free hydrochloric acid is reduced in step (d) using heat, and wherein reducing the level of free hydrochloric acid from the ionic liquid phase comprises:
   heating the ionic liquid phase in the hydrochloric acid removal zone;
   introducing a stripping fluid into the hydrochloric acid removal zone; and
   wherein withdrawing the stream comprising the removed hydrochloric acid comprises withdrawing the stripping fluid comprising the removed hydrochloric acid.

18. The method of claim 16 wherein the level of free hydrochloric acid is reduced in step (d) using the stripping fluid, and wherein reducing the level of free hydrochloric acid from the ionic liquid phase comprises:
   introducing the stripping fluid into the hydrochloric acid removal zone; and
   wherein withdrawing the stream comprising removed hydrochloric acid from the hydrochloric acid removal zone comprises withdrawing a stream of stripping fluid rich in hydrochloric acid from the hydrochloric acid removal zone.

19. The method of claim 16 wherein the level of free hydrochloric acid is reduced in step (d) using liquid-liquid extraction, and wherein reducing the level of free hydrochloric acid in the ionic liquid phase comprises:
   contacting a liquid stream lean in hydrochloric acid with the ionic liquid phase in the hydrochloric acid removal zone; and
   wherein withdrawing the stream comprising removed hydrochloric acid from the removal zone comprises removing a liquid stream rich in hydrochloric acid from the hydrochloric acid removal zone.

20. The method of claim 16 wherein the level of free hydrochloric acid is reduced in step (d) using reduced pressure, and wherein reducing the level of free hydrochloric acid from the ionic liquid phase comprises:
   reducing a pressure in the hydrochloric acid removal zone to a pressure less than a pressure in the separating step (b).

* * * * *